United States Patent [19]

Bigge et al.

[11] Patent Number: 5,179,085
[45] Date of Patent: Jan. 12, 1993

[54] N-SUBSTITUTED α-AMINO ACIDS AND DERIVATIVES THEREOF HAVING PHARMACEUTICAL ACTIVITY

[75] Inventors: Christopher F. Bigge; Graham Johnson, both of Ann Arbor, Mich.

[73] Assignee: Warner-Lambert Company, Morris Plains, N.J.

[21] Appl. No.: 689,726

[22] Filed: Apr. 22, 1991

Related U.S. Application Data

[63] Continuation of Ser. No. 324,351, Mar. 15, 1989, abandoned.

[51] Int. Cl.$^5$ .................. C07F 9/145; C07F 9/117; A61K 31/66
[52] U.S. Cl. .................. 514/114; 514/119; 558/169; 558/170
[58] Field of Search .......... 558/170, 190; 514/114, 514/119

[56] References Cited

U.S. PATENT DOCUMENTS

| | | | |
|---|---|---|---|
| 4,616,005 | 10/1986 | Karanewsky et al. | 514/119 |
| 4,654,429 | 3/1987 | Balthazor et al. | 558/169 |
| 4,746,653 | 5/1988 | Hutchinson et al. | 546/22 |
| 4,918,064 | 4/1990 | Cordi et al. | 514/114 |
| 4,963,539 | 10/1990 | Delaney | 558/170 |

FOREIGN PATENT DOCUMENTS

| | | | |
|---|---|---|---|
| 94186 | 11/1983 | European Pat. Off. | 558/172 |
| 0233154 | 8/1987 | European Pat. Off. | 514/114 |
| 2156818A | 10/1985 | United Kingdom . | |

OTHER PUBLICATIONS

Morrison and Boyd, Organic Chemistry, (Boston, Allen and Bacon, 1979) pp. 738 to 740.

Primary Examiner—Robert T. Bond
Assistant Examiner—E. C. Ward
Attorney, Agent, or Firm—Francis J. Tinney

[57] ABSTRACT

N-substituted α-amino acids and derivatives thereof are described, as well as methods for the preparation and pharmaceutical composition of same, which are useful in selectively blocking the N-methyl-D-aspartate (NMDA) excitatory amino acid receptors in mammals and also are useful in treating cerebrovascular disorders such as cerebral ischemia or cerebral infarction resulting from thromboembolic or hemorrhagic stroke, cerebral vasospasm, hypoglycemia, cardiac arrest, status epilepticus and cerebral trauma as well as for treating schizophrenia, epilepsy, neurodegenerative disorders, Alzheimer's disease or Huntington's disease and also additionally useful as anesthetics in surgical procedures where a finite risk of cerebrovascular damage exists.

6 Claims, No Drawings

N-SUBSTITUTED α-AMINO ACIDS AND DERIVATIVES THEREOF HAVING PHARMACEUTICAL ACTIVITY

This is a continuation of Ser. No. 07/325,351 filed on Mar. 15, 1989, now abandoned.

BACKGROUND OF THE INVENTION

The present invention relates to novel N-substituted α-amino acids and derivatives thereof useful as pharmaceutical agents, to methods for their production, to pharmaceutical compositions which include these compounds, and a pharmaceutically acceptable carrier, and to pharmaceutical methods of treatment. More particularly, the novel compounds of the present invention selectively block the N-methyl-D-aspartate (NMDA) excitatory amino acid receptors in mammals. Thus, the compounds of the present invention are useful for treating diseases responsive to blockade of excitatory amino acid receptors. For example, the compounds of the present invention are useful in the treatment of cerebrovascular disorders such as cerebral ischemia, or cerebral infarction resulting from a range of conditions such as thromboembolic or hemorrhagic stroke, cerebral vasospasm, hypoglycemia, cardiac arrest, status epilepticus, and cerebral trauma. Additionally, the compounds of the present invention are useful in the treatment of schizophrenia, epilepsy, neurodegenerative disorders, Alzheimer's disease or Huntington's disease. Further, the compounds of the present invention are useful as anesthetics, particularly in surgical procedures where a finite risk of cerebrovascular damage exists.

A series of unsaturated amino acids which are antagonists of excitatory amino acid receptors sensitive to NMDA is disclosed in European Patent Application Number 0233154.

A series of substituted α-amino acids which are useful for treating epilepsy, disorders associated with excess GH or LH secretion, schizophrenia, depression, CNS degenerative disorders and cerebral hypoxic conditions is disclosed in Great Britain Patent Number 2156818A.

A series of hetero alkyl phosphonic acid derivatives of 2-piperidine or 2-tetrahydropyridinecarboxylates and esters thereof which are useful for the treatment of disorders responsive to blockade of the NMDA receptors in mammals is disclosed in U.S. Pat. No. 4,746,653.

A series of novel substituted α-amino acids which have utility for treating disorders which benefit from blockade of aspartate and glutamate receptors is disclosed in copending U.S. Ser. No. 256,221, filed Oct. 14, 1988 which is a continuation-in-part of U.S. Ser. No. 126372, filed Nov. 30, 1987.

However, the compounds disclosed in European Patent Application Number 0233154, Great Britain Patent Number 2156818A, U.S. Pat. No. 4,746,653, and copending U.S. Ser. No. 126372 do not suggest or disclose the combination of structural variations of the compounds of the present invention described hereinafter.

SUMMARY OF THE INVENTION

Accordingly, the present invention is a compound of Formula I

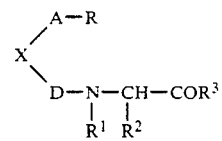

wherein X is —CH$_2$—, —CH$_2$CH$_2$—, —CH=CH—, —NHCO—, —CONH—, —O—, —S—, —SO—, —SO$_2$—,

wherein R$^4$ is hydrogen, lower alkyl, lower alkenyl, aryl or aryl lower alkyl,

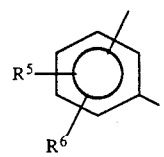

wherein R$^5$ and R$^6$ are independently selected from hydrogen, lower alkyl, aryl, aryl lower alkyl, lower alkoxy, lower alkylthio, halogen, hydroxy, or trifluoromethyl,

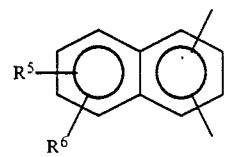

wherein R$^5$ and R$^6$ are as defined above,

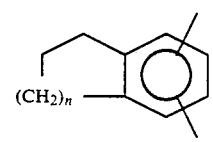

wherein n is 1 to 3, or

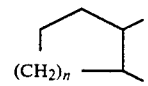

wherein n is as defined above; A and D are independently selected from —(CH$_2$)$_m$—, wherein m is 0 to 3, —CH=CH—, or —CH=CHCH$_2$—;

R is —OPO$_3$R$^7$R$^8$, wherein R$^7$ and R$^8$ are independently selected from hydrogen, lower alkyl, lower alkenyl, aryl, aryl lower alkyl, or a pharmaceutically acceptable labile group, —PO$_3$R$^7$R$^8$, wherein R$^7$ and R$^8$ are as defined above, —PO$_2$R$^7$R$^8$, wherein R$^7$ and R$^8$ are as defined above, —BO$_2$R$^7$R$^8$, wherein R$^7$ and R$^8$ are as defined above, —CO$_2$R$^7$, wherein R$^7$ is as defined above, —SO$_3$R$^7$, wherein R$^7$ is as defined above, or

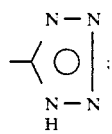

$R^1$ is hydrogen, lower alkyl, lower alkenyl, aryl lower alkyl, —CO—alkyl,

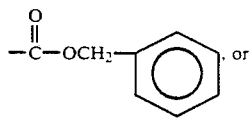, or

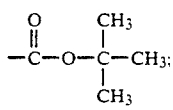

$R_2$ is hydrogen, —CH$_3$, —CH$_2$OH, —CH$_2$—CO$_2$H, —CH$_2$—CONH$_2$, —CH$_2$CH$_2$—CO$_2$H, —CH$_2$CH$_2$—CONH$_2$, —CH$_2$SH,

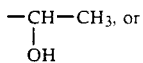

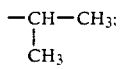

$R_3$ is —OR$^7$, wherein R$^7$ is as defined above, or —NR$^9$R$^{10}$, wherein R$^9$ and R$^{10}$ are independently selected from hydrogen, lower alkyl, lower alkenyl, aryl, aryl lower alkyl, or a pharmaceutically acceptable labile group; or a pharmaceutically acceptable salt thereof.

The compounds of Formula I are useful for the treatment of disorders such as, for example, cerebrovascular disorders in which excitatory amino acids such as, for example, glutamic acid and aspartic acid are implicated. Such disorders comprise cerebral ischemia or cerebral infarction resulting from a range of conditions such as thromboembolic or hemorrhagic stroke, cerebral vasospasm, hypoglycemia, cardiac arrest, status epilepticus, and cerebral trauma. They are also useful for the treatment of schizophrenia, epilepsy, neurodegenerative disorders, Alzheimer's disease or Huntington's disease. A further use of the compounds of Formula I are as anesthetics, particularly in surgical procedures where a finite risk of cerebrovascular damage exists.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "lower alkenyl" means a straight or branched unsaturated hydrocarbon radical having from three to six carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

The term "lower alkoxy" means alkyl-O- of from one to six carbon atoms as defined above for "lower alkyl".

The term "lower alkoxycarbonyloxy lower alkyl means

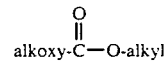

of from one to six carbon atoms as defined above for "lower alkoxy" and "lower alkyl".

The term "lower alkylthio" means alkyl-S- of from one to six carbon atoms as defined above for "lower alkyl".

The term "lower alkanoyloxy" means $$\text{alkyl-}\overset{\overset{\text{O}}{\|}}{\text{C}}\text{—O—}$$

of from one to six carbon atoms as defined above for "lower alkyl".

"Halogen" is fluorine, chlorine, bromine or iodine.

The term "aryl" means a phenyl group or phenyl group substituted by one to four substituents selected from "lower alkyl" of from one to six carbon atoms as defined above for "lower alkyl", "lower alkoxy" of from one to six carbon atoms as defined above for "lower alkoxy", halogen, wherein "halogen" is as defined above or trifluoromethyl.

The term "lower alkoxycarbonyl means

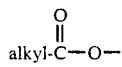

of from one to six carbon atoms as defined above for "lower alkoxy".

The term "aryl lower alkyl" means an aromatic radical as defined above attached to a lower alkyl radical of from one to six carbon atoms as defined above for "lower alkyl".

The term "pharmaceutically acceptable labile group" means a group that may readily be removed under physiological conditions. Thus, in a compound of Formula I wherein R is —OPO$_3$R$^7$R$^8$, —PO$_3$R$^7$R$^8$, —PO$_2$R$^7$R$^8$, —BO$_2$R$^7$R$^8$, —CO$_2$R$^7$, or —SO$_3$R$^7$ and R$^3$ is —OR$^7$ or NR$^9$R$^{10}$ R$^7$ and R$^8$ may be a pharmaceutically acceptable labile group such as amino substituted lower alkyl; mono or di lower alkyl amino substituted lower alkyl; carboxy substituted lower alkyl, e.g., α-carboxy substituted lower alkyl; lower alkoxy carbonyl substituted lower alkyl, e.g., α-lower alkoxycarbonyl substituted lower alkyl; pyridylmethyl; lower alkanoyloxy substituted methyl, e.g., pivaloyloxymethyl; lower alkanoyloxy or lower alkoxy substituted lower alkoxymethyl; bicyclo[2.2.1]heptyloxycarbonyl substituted methyl, e.g., bornyloxycarbonylmethyl; 3-phthalido; lower alkyl, lower alkoxy or halo substituted 3-phthalido; or lower alkoxycarbonyloxy lower alkyl; e.g., 1-methoxy or 1-ethoxycarbonyloxyethyl. Preferably R$^7$ and R$^8$ may be a pharmaceutically acceptable labile group such as lower alkanoyloxy substituted methyl, e.g. pivaloyloxymethyl; di lower alkyl amino alkyl, e.g., 2-diethyl aminoethyl; or pyridylmethyl, e.g., 3-pyridylmethyl.

$R^9$ and $R^{10}$ may be a pharmaceutically acceptable labile group such as di-lower alkylamino-N-lower alkyl such as N-(2-diethylaminoethyl)- or N-(3-diethylaminopropyl)-.

Compounds of Formula I are capable of further forming pharmaceutically acceptable acid addition and/or base salts. All of these forms are within the scope of the present invention. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge, S. M., et al, "Pharmaceutical Salts," *Journal of Pharmaceutical Science,* 66, pp 1-19 (1977)). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorus, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science,* Vol. 66, pp 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers), the racemates as well as the individual enantiomers are intended to be encompassed within the scope of the present invention. Additionally, certain of the compounds of the present invention may exist in a cis- or trans-geometric configuration. The present invention includes both the cis- and the trans-geometric isomers.

A preferred compound of Formula I is one wherein X is $-CH_2-$, $-CH_2CH_2-$, $-CH=CH-$, $-O-$, $-S-$, $-SO-$,

wherein $R^4$ is hydrogen, lower alkyl, lower alkenyl, aryl or aryl lower alkyl, or

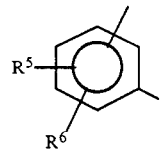

wherein $R^5$ and $R^6$ are independently selected from hydrogen, lower alkyl, aryl, aryl lower alkyl, lower alkoxy, lower alkylthio, halogen, hydroxy or trifluoromethyl;

R is $-PO_3R^7R^8$, wherein $R^7$ and $R^8$ are independently selected from hydrogen, lower alkyl, lower alkenyl, aryl, aryl lower alkyl, or a pharmaceutically acceptable labile group;

$R^2$ is hydrogen, $-CH_3$, or $-CH-CH_3$; and
 |
 $CH_3$ $R^3$ is $-OR^7$, wherein $R^7$ is as defined above.

Another preferred embodiment is a compound of Formula I wherein X is
$-CH_2-$,
$-CH_2CH_2-$,
$-CH=CH-$,
$-S-$,
$-SO-$, or

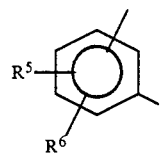

wherein $R^5$ and $R^6$ are independently selected from hydrogen, lower alkyl, aryl, aryl lower alkyl, lower alkoxy, lower alkylthio, halogen, hydroxy or trifluoromethyl; and $R^1$ is hydrogen.

Particularly valuable are:

Methyl N-[[2[(diethoxyphosphinyl)methyl]phenyl]-methyl]glycinate;
Methyl N-[[2-[(diethoxyphosphinyl)methyl]phenyl]methyl]-DL-alaninate;
Methyl N-[[3-[(diethoxyphosphinyl)methyl]phenyl]methyl]glycinate;
Methyl N-[[3-[(diethoxyphosphinyl)methyl]phenyl]methyl]-DL-alaninate;
Methyl N-[[3-[(diethoxyphosphinyl)methyl]phenyl]methyl]-DL-valinate;
Methyl N-[[4-[(diethoxyphosphinyl)methyl]phenyl]methyl]glycinate;
Methyl N-[2-(diethoxyphosphinyl)ethyl]glycinate;
Methyl N-[3-(diethoxyphosphinyl)propyl]glycinate;
(E)-Methyl N-[4-(diethoxyphosphinyl)-2-butenyl]DL-alaninate;
(E)-Ethyl N-[3-[2-(diethoxyphosphinyl)ethenyl]phenyl]glycinate;
Ethyl N-[3-[3-(diethoxyphosphinyl)-1-propenyl]phenyl]glycinate;
Ethyl N-[2-[2-(diethoxyphosphinyl)ethenyl]phenyl]glycinate;
Methyl N-[[3-(diethoxyphosphinyl)phenyl]methyl]glycinate;
Ethyl N-[2-(diethoxyphosphinyl)phenyl]glycinate;
Ethyl N-[3-[3-(diethoxyphosphinyl)propyl]phenyl]glycinate;
Ethyl N-[3-[2-(diethoxyphosphinyl)ethyl]phenyl]glycinate;
Methyl N-[4-(diethoxyphosphinyl)butyl]glycinate;
Ethyl N-[2-[3-[(diethoxyphosphinyl)methyl]phenyl]ethyl]glycinate;
Methyl N-[4-(diethoxyphosphinyl)-3-butenyl]glycinate, mixture of E and Z forms;
(E)-Methyl N-[4-(diethoxyphosphinyl)-2-butenyl]glycinate; and
Methyl N-[2-[[(diethoxyphosphinyl)methyl]thio]ethyl]glycinate; or a pharmaceutically acceptable salt there of;

Most particularly valuable are:
N-[[2-(phosphonomethyl)phenyl]methyl]glycine, hydrochloride;
N-[[2-(phosphonomethyl)phenyl]methyl]-DL-alanine, hydrochloride;
N-[3-(2-phosphonoethyl)phenyl]glycine, monoammonium salt;
N-[(3-phosphonophenyl)methyl]glycine, monohydrochloride;
N-[[3-(phosphonomethyl)phenyl]methyl]glycine, hydrochloride;
N-[[3-(phosphonomethyl)phenyl]methyl]-DL-alanine, hydrochloride;
N-[[3-(phosphonomethyl)phenyl]methyl]-DL-valine, monohydrochloride;
N-[2-[3-(phosphonomethyl)phenyl]ethyl]glycine, monohydrochloride;
N-[[4-(phosphonomethyl)phenyl]methyl]glycine, monohydrochloride;
N-[2-(2-phosphonoethyl)phenyl]glycine, diammonium salt;
N-(2-phosphonophenyl)glycine, diammonium salt;
N-[3-(3-phosphonopropyl)phenyl]glycine, diammonium salt;
N-(2-phosphonoethyl)glycine, monohydrochloride;
N-(3-phosphonopropyl)glycine, monohydrochloride;
N-(4-phosphonobutyl)glycine, monohydrochloride;
N-(4-phosphono-2-butenyl)glycine, monohydrochloride;
N-(4-phosphono-2-butenyl)-DL-alanine, monohydrochloride;
(E)-N-[2-(2-phosphonoethenyl)phenyl]glycine;
(E)-N-[3-(3-phosphono-1-propenyl)phenyl]glycine, ammonium (1:2) salt;
N-(4-phosphono-3-butenyl)glycine, diammonium salt (mixture of E and Z isomers);
N-[2-[(phosphonomethyl)thio]ethyl]glycine, diammonium salt; and
N-[2-[(phosphonomethyl)thio]ethyl]glycine, S-oxide;
or a pharmaceutically acceptable salt thereof;

The compounds of Formula I are valuable in the treatment of cerebrovascular disorders in which excitatory amino acids such as, for example, glutamic acid and aspartic acid are implicated.

The tests employed indicate that compounds of Formula I are capable of blocking the NMDA receptors.

Thus, the compounds of Formula I were tested in vitro for their ability to block NMDA receptors in a binding assay with [$^3$H]3-(2-carboxypiperazin-4-yl)propyl-1-phosphonic acid ([$^3$H]CPP) carried out essentially by a method previously described by Murphy, D. E., et al, *Journal of Pharmacology and Experimental Therapeutics*, Volume 240, pp 778–784 (1987); and for their ability to inhibit glutamate-induced [Ca$^{++}$] influx (GCI) carried out essentially by a method previously described by Marcoux, F. W., et al, "Sigma and Phencyclidine like Compounds as Molecular Probes in Biology", pp 735–746, Domino, E. F. and J. N. Kamenka, eds., NPP Books, Ann Arbor, Michigan, 1988 and Choi, D. W., et al, *Journal of Neuroscience*, Volume 8, pp 185–196 (1988). The aforementioned test methods are incorporated herein by reference. The data in the table shows the NMDA receptor blocking activity of representative compounds of Formula I.

| Biological Activity of Compounds of Formula I (Page 1 of 1) | | | | |
|---|---|---|---|---|
| Example Number | Compound | % Inhibition ($10^{-4}$M) | $^3$H-CPP IC$_{50}$ ($10^{-6}$M) | GCI IC$_{50}$ ($10^{-6}$M) |
| 8d | N-[[3-(Phosphonomethyl)phenyl]methyl]glycine, hydrochloride | | 2.24 | 79 |
| 8g | N-[2-[3-(Phosphonomethyl)phenyl]ethyl]glycine, monohydrochloride | 86 | | |
| 8h | N-[[4-(Phosphonomethyl)phenyl]methyl]glycine, monohydrochloride | | 5.2 | 120 |
| 8o | N-(4-Phosphono-2-butenyl)glycine, monohydrochoride | | 1.2 | 18 |
| 8p | N-(4-Phosphono-2-butenyl)-DL-alanine, monohydrochloride | 58 | | |
| 10a | N-(4-Phosphono-3-butenyl)glycine, diammonium salt (mixture of E and Z isomers) | | 2.45 | |

A compound of Formula I

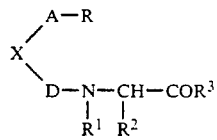 I wherein X is —CH$_2$—, —CH$_2$CH$_2$—, —CH=CH—, —NHCO—, —CONH—, —O—, —S—, —SO—, —SO$_2$—,

wherein R$^4$ is hydrogen, lower alkyl, lower alkenyl, aryl or aryl lower alkyl,

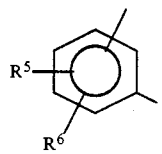

wherein R$^5$ and R$^6$ are independently selected from hydrogen, lower alkyl, aryl, aryl lower alkyl, lower alkoxy, lower alkylthio, halogen, hydroxy, or trifluoromethyl,

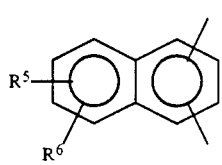

wherein R$^5$ and R$^6$ are as defined above,

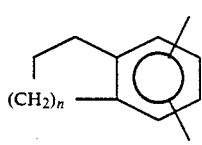

wherein n is 1 to 3, or

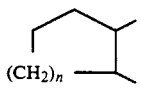

wherein n is as defined above; A and D are independently selected from —(CH$_2$)$_m$—, wherein m is 0 to 3, —CH=CH—, or —CH=CHCH$_2$—;

R is —OPO$_3$R$^7$R$^8$, wherein R$^7$ and R$^8$ are independently selected from hydrogen, lower alkyl, lower alkenyl, aryl, aryl lower alkyl, or a pharmaceutically acceptable labile group, —PO$_3$R$^7$R$^8$, wherein R$^7$ and R$^8$ are as defined above, —PO$_2$R$^7$R$^8$, wherein R$^7$ and R$^8$ are as defined above, —BO$_2$R$^7$R$^8$, wherein R$^7$ and R$^8$ are as defined above, —CO$_2$R$^7$, wherein R$^7$ is as defined above, —SO$_3$R$^7$, wherein R$^7$ is as defined above, or

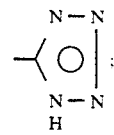

R$^1$ is hydrogen, lower alkyl, lower alkenyl, aryl lower alkyl, —CO—alkyl,

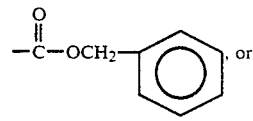 , or

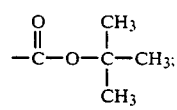

R$_2$ is hydrogen, —CH$_3$, —CH$_2$OH, —CH$_2$—CO$_2$H, —CH$_2$—CONH$_2$, —CH$_2$CH$_2$—CO$_2$H, —CH$_2$CH$_2$—CONH$_2$, —CH$_2$SH,

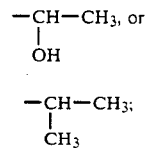

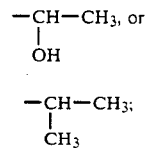

R$_3$ is —OR$^7$, wherein R$^7$ is as defined above, or —NR$^9$R$^{10}$, wherein R$^9$ and R$^{10}$ are independently selected from hydrogen, lower alkyl, lower alkenyl, aryl, aryl lower alkyl, or a pharmaceutically acceptable labile group; or a pharmaceutically acceptable salt thereof may be prepared by reacting a compound of Formula II

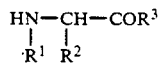 II wherein Z is halogen, CH$_3$C$_6$H$_5$SO$_2$O—, CH$_3$SO$_2$O—, or CF$_3$SO$_2$O— and R, A, X, and D are as defined above with a compound of Formula III

HN—CH—COR$^3$   III
 |    |
 R$^1$  R$^2$ wherein R$^1$, R$^2$, and R$^3$ are as defined above in the presence of a base such as, for example, triethylamine, 4-dimethylaminopyridine, potassium carbonate, sodium carbonate and the like and a solvent such as, for example, methanol, ethanol, dimethylformamide, dimethyl sulfoxide, dimethylacetamide, dioxane, acetonitrile and the like at about 20° C. to about 100° C. for about 15 minutes to about two days to give a compound of Formula I.

Alternatively, a compound of Formula I is prepared by reacting a compound of Formula IV

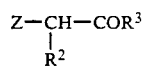 IV wherein Z, R$^2$, and R$^3$ are as defined above with a compound of Formula V

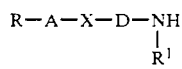  V wherein R, A, X, D, and $R^1$ are as defined above using the methodology previously described for preparing a compound of Formula I from a compound of Formula II and a compound of Formula III to give a compound of Formula I.

Preferably a compound of Formula Ia

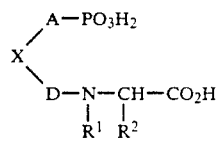  Ia wherein A, X, D, $R^1$ and $R^2$ are as defined above is prepared by reacting a compound of Formula Ib

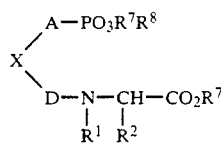  Ib wherein A, X, D, $R^1$, $R^2$, $R^7$, and $R^8$ are as defined above with an acid such as, for example, hydrochloric acid or alternatively a two step procedure using a trialkylsilyl halide such as, for example, trimethyl silyl bromide in a solvent such as, for example, acetonitrile, diethyl ether, and the like and then a basic solution of potassium hydroxide, sodium hydroxide in water or potassium trimethylsilanolate in a solvent such as, for example, acetonitrile, diethyl ether, and the like to give a compound of Formula Ia.

A compound of Formula V is prepared from a compound of Formula II

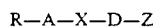  II wherein R, A, X, D, and Z are as defined above and a compound of Formula VI

  VI wherein $R^1$ is as defined above using the methodology previously described for preparing a compound of Formula I from a compound of Formula II and a compound of Formula III to give a compound of Formula V.

A compound of Formula Ib is prepared from a compound of Formula VII

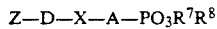  VII wherein Z, D, X, A, $R^7$, and $R^8$ are as defined above and a compound of Formula VIII

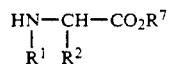  VIII wherein $R^1$, $R^2$, and $R^7$ are as defined above using the methodology previously described for preparing a compound of Formula I from a compound of Formula II and a compound of Formula III to give a compound of Formula Ib.

Preferably, a compound of Formula Ic

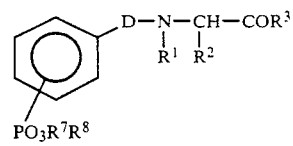  Ic wherein D, $R^1$, $R^2$, $R^3$, $R^7$, and $R^8$ are as defined above may be prepared by reacting a compound of Formula IX

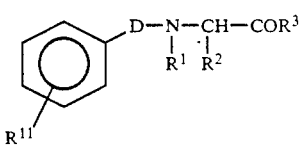  IX wherein $R^{11}$ is bromo, iodo, HgCl or $CF_3SO_2O-$ and D, $R^1$, $R^2$, and $R^3$ are as defined above with a compound of Formula X

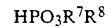  X wherein $R^7$ and $R^8$ are as defined above in the presence of a catalyst such as, for example, tetrakis (triphenylphosphine) palladium (0) and the like, a solvent such as, for example, dimethylformamide, toluene, benzene, acetonitrile and the like, and a base such as, for example, triethylamine and the like at about 20° C. to about 150° C. for about 15 minutes to about 24 hours to give a compound of Formula Ic.

Preferably, a compound of Formula Id

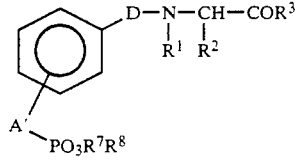  Id wherein A' is $-CH=CH-$ or $-CH=CH-CH_2$ and D, $R^1$, $R^2$, $R^3$, $R^7$, and $R^8$ are as defined above may be prepared by reacting a compound of Formula IX with an appropriate phosphonate reagent such as, for example, dimethyl vinylphosphonate, diethyl vinylphosphonate, diphenyl vinylphosphonate, dibenzyl vinylphosphonate, dimethyl allylphosphonate, diethyl allylphosphonate, diphenyl allylphosphonate, dibenzyl allylphosphonate, and the like in the presence of a catalyst such as, for example, bis(triphenylphosphine) palladium (II) chloride, bis(triphenylphosphine)palladium (II) acetate, lithium tetrachloropalladate (II) and the like, a solvent such as, for example, dimethylformamide, methanol, ethanol, water, tetrahydrofuran, toluene, benzene, acetonitrile and the like and a base such as, for example, triethylamine and the like at about 20° C. to about 150° C. for about 15 minutes to about 24 hours to give a compound of Formula Id.

Preferably, a compound of Formula Ie

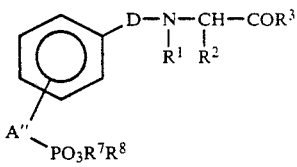

wherein A″ is —CH$_2$CH$_2$— or —CH$_2$CH$_2$CH$_2$ and D, R$^1$, R$^2$, R$^3$, R$^7$, and R$^8$ are as defined above may be prepared by reduction of a compound of Formula Id with hydrogen in the presence of a catalyst such as, for example, palladium on carbon and the like and a solvent such as, for example, ethanol and the like to give a compound of Formula Ie.

Preferably, a compound of Formula If

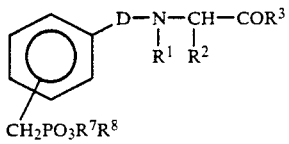

wherein D, R$^1$, R$^2$, R$^3$, R$^7$, and R$^8$ are as defined above may be prepared by reacting a compound of Formula XI

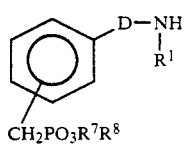

wherein D, R$^1$, R$^7$, and R$^8$ are as defined above with a compound of Formula IV using the methodology previously described for preparing a compound of Formula I from a compound of Formula II and a compound of Formula III to give a compound of Formula If.

A compound of Formula IX may be prepared by reacting a compound of Formula XII

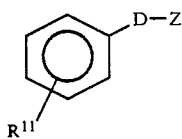

wherein D, Z, and R$^{11}$ are as defined above with a compound of Formula III using the methodology previously described for preparing a compound of Formula I from a compound of Formula II and a compound of Formula III to give a compound of Formula IX.

A compound of Formula XI may be prepared by reacting a compound of Formula XIII

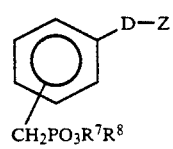

wherein D, Z, R$^7$, and R$^8$ are as defined above with a compound of Formula VI using the methodology previously described for preparing a compound of Formula I from a compound of Formula II and a compound of Formula III to give a compound of Formula XI.

A compound of Formula XIII may be prepared by reacting a compound of Formula XIV

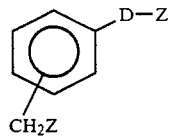

wherein D and Z are as defined above with a compound of Formula XV

wherein R$^{12}$ is lithium, potassium, sodium and the like in a solvent such as, for example, tetrahydrofuran, diethyl ether, dimethylformamide, dimethylacetamide, dimethyl sulfoxide and the like at about $-78°$ C. to about 60° C. for about 15 minutes to about 24 hours to give a compound of Formula XIII.

Alternatively, a compound of Formula XIII may be prepared by reacting a compound of Formula XIV with a compound of Formula X in a solvent such as, for example, toluene, benzene, acetonitrile, dimethylformamide and the like at about 20° C. to about 150° C. for about 15 minutes to about 24 hours to give a compound of Formula XIII.

Preferably, a compound of Formula Ig

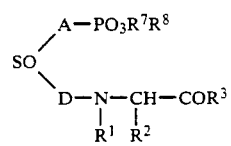

wherein A, D, R$^1$, R$^2$, R$^3$, R$^7$, and R$^8$ are as defined above is prepared by oxidation of a compound of Formula Ih

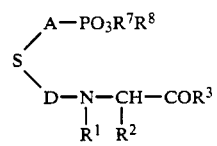

wherein A, D, R$^1$, R$^2$, R$^3$, R$^7$, and R$^8$ are as defined above with an oxidizing reagent such as, for example, a peroxy acid such as meta-chloroperbenzoic, hydrogen peroxide, preferably a 30% aqueous solution, tertiary-butyl hydroperoxide, iodobenzene dichloride, sodium periodate, potassium permanganate, and the like in a solvent such as, for example dichloromethane, water and the like at about 0° to about 50° C. for about 15 minutes to about two days to give a compound of Formula Ig.

Preferably a compound of Formula Ii

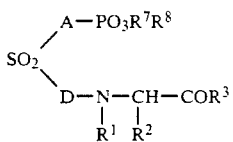

wherein A, D, $R^1$, $R^2$, $R^3$, $R^7$, and $R^8$ are as defined above is prepared by oxidation of a compound of Formula Ih with at least two equivalents of an oxidizing reagent as previously described for preparing a compound of Formula Ig from a compound of Formula Ih to give a compound of Formula Ii.

Preferably, a compound of Formula Ih is prepared by reacting a compound of Formula XVI

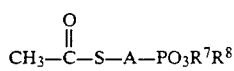

wherein A, $R^7$, and $R^8$ are as defined above with a compound of Formula XVII

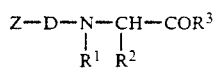

wherein Z, D, $R^1$, $R^2$, and $R^3$ are as defined above in the presence of a nucleophilic base such as, for example, sodium methoxide, sodium ethoxide and the like and a solvent such as, for example, methanol, ethanol, tetrahydrofuran, diethyl ether, dimethylformamide, dimethyl sulfoxide and the like at about 0° C. to about 150° C. for about 15 minutes to about two days to give a compound of Formula Ih.

A compound of Formula XVI is prepared by reacting a compound of Formula XVIII

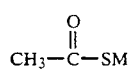

wherein M is potassium, sodium, lithium or tetra n-butylammonium with a compound of Formula XIX

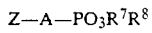

wherein Z, A, $R^7$, and $R^8$ are as defined above in the presence of a solvent such as, for example, tetrahydrofuran, diethyl ether, dimethylformamide, acetonitrile, and the like at about 0° C. to about 100° C. for about 15 minutes to about two days to give a compound of Formula XVI.

A compound of Formula XVII is prepared by reacting a compound of Formula XX

wherein Z and D are as defined above with a compound of Formula III in the presence of a base such as, for example, triethylamine, 4-dimethylaminopyridine, potassium carbonate, sodium carbonate and the like and a solvent such as, for example, methanol, ethanol, dimethylformamide, dimethyl sulfoxide, dioxane, tetrahydrofuran and the like at about 25° C. to about 100° C. to give a compound of Formula XVII.

A compound of Formula I, which is a racemic mixture, may be separated by conventional means such as, for example, by fractional crystallizations of optically active sat forms or by chromatography. Alternatively, a pure enantiomeric or diastereoisomeric form may be produced by utilizing optically active starting materials.

A compound of Formula I, which is a cis- trans mixture can be separated in a known manner into the corresponding cis and trans components.

Compounds of Formula II, Formula III, Formula IV, Formula VI, Formula VII, Formula VIII, Formula X, Formula XII, Formula XIV, Formula XV, Formula XVIII, Formula XIX, and Formula XX are either known or capable of being prepared by methods known in the art.

In the aforementioned processes for the preparation of compounds of Formula I protecting groups may be employed in the preparation of a compound of Formula I, such protecting groups as well as methods for incorporation and removal of these protecting groups are discussed in "The Peptides. Analysis, Structure, Biology", Gross, E., and Meinhofer, J., eds, Academic Press, New York, New York, Volume 3, 1981 and "Protective Group in Organic Synthesis", Greene, T. W., John Wiley & Sons, New York, New York, 1981.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, Cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 500 mg preferably 5 mg to 100 mg according to the particular application and the potency of the active component. The composition can, if desired, also contain other compatible therapeutic agents.

In therapeutic use as agents for treating cerebrovascular disorders in which excitatory amino acids such as, for example, glutamic acid and glutamic acid are implicated, the compounds utilized in the pharmaceutical method of this invention are administered at the initial dosage of about 0.01 to about 100 mg per kilogram daily. A daily dose range of about 0.05 to about 50 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

Methyl N[[2[(diethoxyphosphinyl)methyl]phenyl]methyl]-glycinate.

A solution of the diethyl[[2(bromomethyl)phenyl]-methyl]phosphonate (Example A) (0.9 g, 2.8 mmol) in methanol (25 ml) and triethylamine (5 ml) is treated with glycine methyl ester hydrochloride (0.71 g, 5.6 mmol) and heated at reflux in an oil bath for 19 hours. The solvent is removed in vacuo and the residue dissolved in water and extracted with chloroform. The chloroform layer is dried over magnesium sulfate, filtered, and evaporated. The oily residue is purified via silica gel chromatography (2–4% methanol in chloroform as eluant).

$^1$H-NMR (Nuclear Magnetic Resonance): 4H, m, 7.35–7.2 ppm; 6H, m, 4.1–3.7; 3H, s, 3.65; 2H, s, 3.37; 2H, d, 3.31; 1H, br.s, 2.35; 6H, t, 1.22.

In a process analogous to Example 1 using appropriate starting materials the corresponding compounds of Formula I are prepared:

EXAMPLE 1a

Methyl N-[[2-[(diethoxyphosphinyl)methyl]phenyl]methyl]-DL-alaninate.

$^1$H-NMR (CDCL$_3$): 4H, br s, 7.35–7.1 ppm: 4H, m, 4.1–3.7; 5H, s, 3.67; 1H, q, 3.33; 2H, d, 3.33; 1H, br s, 1.97; 9H, m, 1.4–1.05.

EXAMPLE 1b

Methyl N-[[3[(diethoxyphosphinyl)methyl]phenyl]methyl]-glycinate.

$^1$H-NMR: 4H, m, 7.26–7.21 ppm; 4H, m, 4.06–3.92; 2H, s, 3.77; 3H, s, 3.71; 2H, s, 3.40; 2H, d, 3.12; 6H, t, 1.22.

EXAMPLE 1c

Methyl N-[[3-[(diethoxyphosphinyl)methyl]phenyl]methyl]DL-alaninate.

$^1$H-NMR: 4H, br. s, 7.17 ppm; 4H, m, 4.2–3.75; 5H, s, 3.7; 1H, m, 3.5–3.2; 2H, d, 3.06; 1H, br. s, 2.83; 6H, m, 1.35–1.05.

EXAMPLE 1d

Methyl N-[[3-[(diethoxyphosphinyl)methyl]phenyl]methyl]DL-valinate.

$^1$H-NMR: 4H, m, 7.17 ppm; 4H, m, 4.1–3.77; 3H, s, 3.67; 1H, m, 3.7–3.4; 2H, m, 3.4–2.9; 2H, d, 3.07; 2H, m, 2.0–1.65; 6H, t, 1.2; 6H, d, 0.9.

EXAMPLE 1e

Methyl N-[[4-[(diethoxyphosphinyl)methyl]phenyl]methyl]-glycinate.

$^1$H-NMR: 4H, s, 7.2 ppm; 4H, m, 4.12–3.8; 2H, s, 3.72; 3H, s, 3.67; 2H, s, 3.35; 2H, d, 3.1; 6H, t, 1.2.

EXAMPLE 1f

Methyl N-[2(diethoxyphosphinyl)ethyl]glycinate.

$^1$H-NMR: 4H, m, 4.24–4.03 ppm; 2H, s, 3.73; 3H, s, 3.40: 2H, m, 2.98–2.83; 3H, m, 2.06–1.85; 6H, t, 1.28.

EXAMPLE 1g

Mixture of Ethyl & Methyl N-[3-(diethoxyphosphinyl)propyl]glycinate.

$^1$H-NMR: 4H, m, 4.24–4.01 ppm; 3H, s, 3.72; 2H, s, 3.38; 2H, t, 2.67; 4H, m, 2.70–2.64; 6H, t, 1.31.

EXAMPLE 1h (E)-Methyl N-[4-(diethoxyphosphinyl)-2-butenyl]-DL-alaninate.

$^1$H-NMR: (Z/E) 2H, m, 5.59–5.50 ppm; 4H, m, 4.08–3.97; 3H, s, 3.65; 1H, q, 3.29; 2H, m, 3.22–3.04; 2H, m, 2.57–2.46; 1H, br. s, 1.60; 9H, m, 1.29–1.20.

EXAMPLE 2

(E)-Ethyl N-[3-[2-(diethoxyphosphinyl)ethenyl]phenyl]glycinate.

A solution of ethyl N-(3-bromophenyl)glycinate (Example B) (4 g, 15.5 mmol), diethyl vinylphosphonate (4.92 g, 30 mmol), and bis(triphenylphosphine) palladium (II) chloride (1 g) in dimethylformamide (15 ml) and triethyamine (5 ml) is immersed in an oil bath (95° C.) and stirred for 20 hours. After cooling the dimethylformamide is removed in vacuo and the oily brown residue is dissolved in a saturated solution of sodium chloride and extracted with chloroform. The chloroform layer is dried over magnesium sulfate, filtered and evaporated to give a residue (3.2 g). Purification is accomplished by silica gel chromatography (ethyl acetate as eluant, a single fluorescent spot on tlc, Rf=0.5 (ethyl acetate)).

$^1$H-NMR: 4H, m, 7.71–6.92 ppm; 2H, m, 6.89–6.13; 2H, q 4.13; 4H, m, 4.10–4.03; 2H, s, 3.92; 9H, m, 1.38–1.23.

In a process analogous to Example 2 using appropriate starting materials the corresponding compounds of Formula I are prepared:

EXAMPLE 2a

Ethyl N-[3-[3-(diethoxyphosphinyl)-1-propenyl]phenyl]glycinate.

$^1$H-NMR: (Z/E) 4H, m, 7.71–6 41 ppm; 1H, m, 6.20–5.71; 1H, m, 5.27–5.18; 2H, q, 4.25; 4H, m, 4.17–3.97; 2H, s, 3.91; 2H, m, 2.81–2.56; 9H, m, 1.35–1.25.

EXAMPLE 2b

Ethyl N-[2-[2-(diethoxyphosphinyl)ethenyl]phenyl]glycinate.

$^1$H-NMR: 3H, m, 7.85–7.25 ppm; 1H, t, 6.78; 1H, d, 6.54; 1H, dd, 6.19; 2H, q, 4.25; 4H, m, 4.17–4.06; 2H, s, 3.94; 9H, m, 1.42–1.23.

EXAMPLE 3

Methyl N-[[3-(diethoxyphosphinyl)phenyl]methyl]glycinate.

A solution of diethylphosphite (1 ml, 6.75 mmol) and triethylamine (5 ml) is stirred under a nitrogen atmosphere and then treated with tetrakis (triphenylphosphine) palladium (0) (0.4 g). A solution of methyl N-[(3-bromophenyl)methyl]glycinate (Example C) (1.62 g, 6.28 mmol) in toluene (10 ml) is degassed in vacuo, added to the palladium catalyst mixture, and the reaction vessel immersed in a 105° C. oil bath for 17 hours. The reaction mixture is cooled to room temperature and diluted with diethyl ether. An insoluble precipitate is removed by filtration and the filtrate evaporated to give a yellow residue. The product is purified by chromatography on silica gel (0–5% methanol in chloroform as eluant). $^1$H-NMR: 4H, m, 7.9–7.3 ppm; 4H, m, 4.25–3.95; 2H, s, 3.8; 3H, s, 3.7; 2H, s, 3.4; 6H, t, 1.25.

In a process analogous to Example 3 using appropriate starting materials the corresponding compound of Formula I is prepared:

EXAMPLE 3a

Ethyl N-[2-(diethoxyphosphinyl)phenyl]glycinate.

$^1$H-NMR: 4H, m, 7.67–6.95 ppm; 1H, t, 6.33; 6H, m, 4.25–3.9; 2H, d, 3.8; 9H, m, 1.4–1.15.

EXAMPLE 4

Ethyl N-[3-[3-(diethoxyphosphinyl)propyl]phenyl]glycinate.

A solution of ethyl N-[3-[3-(diethoxyphosphinyl)1-propenyl]phenyl]glycinate (Example 2a) in ethanol (75 ml) is treated with 10% palladium on carbon (0.25 g) and shaken on a Parr apparatus under a hydrogen atmosphere (50 pounds per square inch (psi)). After filtration, the filtrate is evaporated and the residue purified over silica gel (ethyl acetate as eluant) to give 1.24 g of a clear oil.

$^1$H-NMR: 1H, s, 7.27 ppm; 1H, t, 7.14; 2H, m, 6.67–6.57; 2H, q, 4.25; 4H, m, 4.16–4.02; 2H, s, 3.92; 2H, t, 2.63; 4H, m, 2.0–1.60; 9H, m, 1.35–1.26.

In a process analogous to Example 4, using appropriate starting materials, the corresponding compounds of Formula I are prepared:

EXAMPLE 4a

Ethyl N-[3-[2-(diethoxyphosphinyl)ethyl]phenyl]glycinate.

$^1$H-NMR: 1H, dd, 7.11 ppm; 1H, d, 6.60; 2H, m, 6.47–6.45; 2H, q, 4.25; 4H, m, 4.18–4.03; 2H, d, 3.89; 2H, m, 2.89–2.78; 2H, m, 2.10–1.97; 9H, m, 1.35–1.20.

EXAMPLE 4b

Methyl N-[4(diethoxyphosphinyl)butyl]glycinate.

$^1$H-NMR: 4H, m, 4.17–4.02 ppm; 3H, s, 3.81; 2H, s, 3.76; 2H, t, 3.01; 6H, m, 2.04–1.64; 6H, t, 1.33.

EXAMPLE 4c

Ethyl N-[2-[2-(diethoxyphosphinyl)ethyl]phenyl]glycinate.

$^1$H-NMR: 2H, m, 7.17–7.06 ppm; 1H, t, 6.72; 1H, d, 6.50; 2H, q, 4.24; 4H, m, 4.16–4.06; 1H, d, 3.94; 2H, m, 2.89–2.79; 2H, s, 2.05; 2H, m, 1.79–1.66; 9H, m, 1.36–1.09.

EXAMPLE 5

Ethyl N-[2-[3-[(diethoxyphosphinyl)methyl]phenyl]ethyl]glycinate.

A solution of diethyl [[3-(2-aminoethyl)phenyl]methyl]phosphonate (Example D) (3.6 g, 13.2 mmol) in toluene (15 ml) and triethylamine (2.7 g, 26.4 mmol) is cooled in an ice/salt bath and a solution of ethyl bromoacetate (2.2 g, 13.2 mmol) in toluene (8 ml) is added dropwise over 20 minutes. A gum forms and methanol (5 ml) is added and stirred an additional two hours. After evaporation of the solvent, the residue is dissolved in ethyl acetate (75 ml) and washed with water (20 ml, and 10 ml) and then saturated sodium chloride solution (10 ml). The organic layer is dried over magnesium sulfate, filtered, and evaporated to give an oil (4.3 g). Chromatography over silica gel gives an analytical, colorless oil. $^1$H-NMR: 4H, m, 7.33–7.0 ppm; 6H, m, 4.33–3.86; 2H, s, 3.40; 2H, d, 3.13; 4H, m, 2.90–2.70; 1H, s, 1.8; 9H, m, 1.33–1.10.

EXAMPLE 6

Methyl N-[4-(diethoxyphosphinyl)-3-butenyl]glycinate, Mixture of E and Z Forms.

A solution of 4-(diethylphosphonyl)-3-butenyl methanesulfonate, mixture of E and Z forms (Example F) (2.9 g, 10.1 mmol) and glycine methyl ester hydrochloride (1.4 g, 11.1 mmol) and 4-dimethylaminopyridine (0.05 g) in ethanol (20 ml) and triethylamine (2 ml) is heated at reflux for 20 hours. The solvent is removed in vacuo and the residue dissolved in water and extracted with chloroform (3×30 ml). The chloroform layer is dried over magnesium sulfate, filtered and evaporated to give a yellow oil (2.2 g). Chromatography over silica gel (0–5% methanol in chloroform as eluant) gives a clear oil (0.3 g). $^1$H-NMR: (Z/E) 1H, m, 6.71–6.42 ppm; 1H, m, 5.82–5.56; 4H, m, 4.23–3.94; 2H, s, 3.73; 2H, m, 3.45–3.39; 2H, m, 2.80–2.77; 1H, br. s, 2.21; 6H, m, 1.36–1.24.

EXAMPLE 7

(E)-Methyl N-[4-(diethoxyphosphinyl)-2-butenyl]glycinate.

A solution of glycine methyl ester hydrochloride (1.6 g, 12.7 mmol) and diethyl (4-bromo-2-butenyl)phosphonate (Example E) (3.14 g, 11.6 mmol) in methanol and triethylamine (5 ml) is heated at reflux for 16 hours. The solvent is removed in vacuo and the residue dissolved in water and extracted with chloroform (2×70 ml). The organic layer is dried over magnesium sulfate, filtered and evaporated. The residue is purified over silica gel (0–2.5% methanol in chloroform as eluant) to give 1.1 g of a clear oil.

$^1$H-NMR: 2H, m, 5.69–5.59 ppm; 4H, m, 4.18–4.02; 3H, s, 3.73; 2H, s, 3.40; 2H, m, 3.30–3.19; 2H, dd, 2.59; 1H, br. s, 1.66; 6H, t, 1.31.

EXAMPLE 8

N-[[2-(Phosphonomethyl)phenyl]methyl]glycine, hydrochloride.

A solution of methyl N-[[2[(diethoxyphosphinyl)methyl]phenyl]methyl]glycinate (Example 1) (0.5 g, 1.5 mmol) in 6N hydrochloric acid solution (10 ml) is stirred at reflux in an oil bath for 18 hours. The water is removed in vacuo to give 0.4 g of a white solid.

$^1$H-NMR: 4H, m, 7.57–7.33 ppm; 2H, s, 4.33; 2H, s, 3.97; 2H, d, 3.28.

In a process analogous to Example 8 using appropriate starting materials the corresponding compounds of Formula I are prepared:

EXAMPLE 8a

N-[[2-(Phosphonomethyl)phenyl]methyl]-DL-alanine, hydrochloride.

$^1$H-NMR: 4H, m, 7.51–7.33 ppm; 2H, m, 4.40–4.22; 1H, q, 4.11; 2H, d, 3.27; 3H, d, 1.61.

EXAMPLE 8b

N-[3-(2-Phosphonoethyl)phenyl]glycine, monoammonium salt.

$^1$H-NMR: 1H, t, 7.21 ppm; 2H, m, 6.90–6.69; 1H, dd, 6.57; 2H, s, 3.72; 2H, m, 2.80–2.70; 2H, m, 1.79–1.66.

EXAMPLE 8c

N-(3-Phosphonophenyl)methyl]glycine, monohydrochloride.

$^1$H-NMR: 2H, m, 7.85–7.80 ppm; 2H, m, 7.64–7.59; 2H, s, 4.38; 2H, s, 3.98.

EXAMPLE 8d

N-[[3-(Phosphonomethyl)phenyl]methyl]glycine, hydrochloride.

$^1$H-NMR: 4H, m, 7.47–7.41 ppm; 2H, s, 4.31; 2H, s, 3.95; 2H, d, 3.21.

EXAMPLE 8e

N-[[3-(Phosphonomethyl)phenyl]methyl]-DL-alanine, hydrochloride.

$^1$H-NMR: 4H, m, 7.46–7.37 ppm; 2H, s, 4.28; 1H, q, 4.07; 2H, d, 3.18; 3H, d, 1.60.

EXAMPLE 8f

N-[[3-(Phosphonomethyl)phenyl]methyl]-DL-valine, monohydrochloride.

$^1$H-NMR: 4H, br. s, 7.4 ppm; 2H, s, 4.3; 1H, d, 3.85; 2H, d, 3.2; 1H, m, 2.5–2.1; 6H, t, 1.0.

EXAMPLE 8g

N-[2-[3-(Phosphonomethyl)phenyl]ethyl] glycine, monohydrochloride; mp 175°–180° C.

$^1$H-NMR: 4H, m, 7.5–7.15 ppm; 2H, s, 3.93; 3H, m, 3.50–3.23; 3H, m; 3.2–2.9.

EXAMPLE 8h

N-[[4-(Phosphonomethyl)phenyl]methyl]glycine, monohydrochloride.

$^1$H-NMR: 4H, s, 7.4 ppm; 2H, s, 4.2; 2H, s, 3.95; 2H, d, 3.15.

EXAMPLE 8i

N-[2-(2-Phosphonoethyl)phenyl]glycine, with ammonia (1:2).

Alternative Preparation of N-[2-(2-Phosphonoethyl)phenyl]glycine, with ammonia (1:2).

A solution of ethyl N-[2-[2-(diethoxyphosphinyl)ethyl]phenyl]glycinate (Example 4c) (0.8 g, 2.3 mmol) in acetonitrile (10 ml) is stirred under nitrogen and treated with trimethylsilyl bromide (3 ml). After 20 hours the solvent is removed and the residue dissolved in water (10 ml) and potassium hydroxide (0.39 g, 6.9 mmol) added to the reaction and the mixture stirred for 23 hours. Purification on Dowex 50×400 gives 0.46 g of a light tan foam. $^1$H-NMR: 4H, m, 7.21–6.76 ppm; 2H, s, 3.75; 2H, m, 2.80–2.66; 2H, m, 1.76–1.63.

EXAMPLE 8j

N-(2-Phosphonophenyl)glycine, with ammonia (1:2).

$^1$H-NMR: 2H, d, 7.36 ppm; 2H, d, 6.64; 2H, s, 3.70.

EXAMPLE 8k

N-[3-(3-Phosphonopropyl)phenyl]glycine, diammonium salt.

$^1$H-NMR: 1H, s, 7.27 ppm; 1H, t, 7.14; 2H, m, 6.67–6.57; 2H, s, 3.93; 2H, t, 2.63; 4H, m, 1.90–1.60.

EXAMPLE 8l

N-(2-Phosphonoethyl)glycine, monohydrochloride.

$^1$H-NMR: 2H, m, 7.26–7.22 ppm; 1H, t, 7.15; 1H, t, 6.85; 2H, s, 3.78; 2H, m, 2.83–2.73; 2H, m, 1.86–1.70.

EXAMPLE 8m

N-(3-Phosphonopropyl)glycine, monohydrochloride.

EXAMPLE 8n

N-(4-Phosphonobutyl)glycine, monohydrochloride.

$^1$H-NMR: 2H, s, 3.94 ppm; 2H, t, 3.14; 6H, m, 1.88–1.61.

EXAMPLE 8o

N-(4-Phosphono-2-butenyl)glycine, monohydrochloride.

$^1$H-NMR: 1H, m, 6.08–5.97 ppm; 1H, m, 5.77–5.61; 2H, s, 3.97; 2H, dd, 3.73; 2H, m, 2.71–2.57.

EXAMPLE 8p

N-(4-Phosphono-2-butenyl)-DL-alanine, monohydrochloride.

$^1$H-NMR: (Z/E) 1H, m, 6.07–5.95 ppm; 1H, m, 5.75–5.60; 1H, q, 3.95; 2H, m, 3.8–3.67; 2H, m, 2.65–2.50; 3H, d, 1.54.

EXAMPLE 9

(E)-N-[2-(2-Phosphonoethenyl)phenyl]glycine.

A solution of ethyl N-[2-[2-(diethoxyphosphinyl)ethenyl]phenyl]glycinate (Example 2b)(1.3 g, 3.8 mmol) in diethyl ether (15 ml) is treated with potassium trimethylsilanoate (0.54 g, 4.2 mmol) and stirred over the weekend. The diethyl ether is removed and the oily residue suspended in acetonitrile (50 ml) and stirred under a nitrogen atmosphere for 30 minutes and further treated with trimethylsilylbromide (3 ml) and stirred at room temperature for four hours. $^1$H-NMR indicates some ester remains so the acetonitrile is removed and the residue is treated with a solution of potassium hydroxide (0.56 g, 10 mmol) in water (3 ml) and stirred for 16 hours. The water is removed and the residue purified on Dowex 50×400 ion exchange resin (water and 2N ammonium hydroxide as eluants). The desired material (fluorescent on tlc under uv light, ninhydrin positive) is obtained from the water eluate as a light, green-white solid (0.12 g).

$^1$H-NMR: 3H, m, 7.58–7.33 ppm; 1H, t, 7.05; 1H, d, 6.88; 1H, dd, 6.44; 2H, s, 4.09.

EXAMPLE 10

(E)-N-[3-(3-Phosphono-1-propenyl)phenyl]glycine, ammonium (1:2) salt.

A solution of ethyl N-[3-[3-(diethoxyphosphinyl)1-propenyl]phenyl]glycinate (Example 2a)(0.35 g, 0.98 mmol) in acetonitrile (15 ml) is treated under a nitrogen atmosphere with trimethylsilyl bromide (2 ml). After two days at room temperature, the solvent is evaporated and the residue suspended in an aqueous solution of sodium hydroxide (10 ml, three equivalents) and stirred two days. The solution is neutralized to pH 5 and purified on Dowex 50×400 ion exchange resin (water and 2N ammonium hydroxide as eluants). $^1$H-NMR: 1H, t, 7.23 ppm, 1H, d, 6.92; 1H, s, 6.80; 1H, d, 6.62; 2H, m, 6.49–6.29; 2H, s, 3.73; 2H, dd, 2.54.

In a process analogous to Example 10, using appropriate starting materials, the corresponding compound of Formula I is prepared:

EXAMPLE 10a

N-[4-Phosphono-3-butenyl)glycine, diammonium salt. (Mixture of E and Z isomers).

$^1$H-NMR: 2H, m, 6.04–5.80 ppm; 2H, s, 3.56; 2H, t, 3.20; 2H, m, 2.90–2.75.

EXAMPLE 11

Methyl N-[2-[[(diethoxyphosphinyl)methyl]thio]ethyl]glycinate

A suspension of potassium carbonate (0.42 g, 3 mmol) in anhydrous dimethylformamide (3 ml) is treated with glycine methyl ester hydrochloride (0.25 g, 2 mmol) and stirred under nitrogen. After 5 minutes diethyl (2-bromoethyl)thiomethylphosphonate (Example G) (0.28 g, 1.08 mmol) is added as a solution in dimethylformamide (0.5 ml). After stirring 48 hours, the dimethylformamide is removed in vacuo, and the residue is dissolved in water and extracted with chloroform (2×30 ml). The organic layer is separated, dried over sodium sulfate, filtered, evaporated, and the residue is purified by silica gel chromatography (60:1 chloroform:methanol as eluant) to give methyl N-[2-[[(diethoxyphosphinyl)methyl]thio]ethyl]glycinate.

$^1$H-NMR: 4H, m, 4.27–3.93 ppm; 3H, s, 3.67; 2H, s, 3.38; 4H, br.s, 2.82; 2H, d, 2.77; 1H, m, 2.15–2.0; 6H, t, 1.30.

EXAMPLE 12

N-[2-[(Phosphonomethyl)thio]ethyl]glycine, diammonium salt.

A solution of methyl-N-[2-[[(diethoxyphosphinyl)methyl]thio]ethyl]glycinate (Example 11) is hydrolyzed in 6N hydrochloric acid solution using the procedure described in Example 8 to give N-[2-[(phosphonomethyl)thio]ethyl]glycine. The compound is purified on Dowex 50×400 ion exchange resin (2N ammonium hydroxide as eluant) to give the diammonium salt.

$^1$H-NMR: 2H, s, 3.62 ppm; 2H, t, 3.29; 2H, t, 2.94; 2H, d, 2.56.

EXAMPLE 13

N-[2-[(Phosphonomethyl)thio]ethyl]glycine, S-oxide.

A solution of N-[2-[(phosphonomethyl)thio]ethyl]glycine, diammonium salt (Example 12) in water (0.5 ml) is treated with a 30% solution of hydrogen peroxide (0.1 ml) and stirred overnight. Lyophilization gives N-[2-[(phosphonomethyl)thio]ethyl]glycine, S-oxide.

$^1$H-NMR: 2H, s, 3.71; 2H, m, 3.78-3.43; 2H, d, 3.30; 2H, m, 3.3-3.1.

PREPARATION OF STARTING MATERIALS

EXAMPLE A

Diethyl[[2-(bromomethyl)phenyl]methyl]phosphonate.

A suspension of sodium hydride (60% in oil, 1.4 g, 35 mmol) in anhydrous tetrahydrofuran (75 ml) is stirred under a nitrogen atmosphere and a solution of diethylphosphite (4.82 g, 34.9 mmol) in tetrahydrofuran (20 ml) is added dropwise. The reaction mixture is stirred an additional 20 minutes. A solution of 1,2-bis(bromomethyl)benzene (10.56 g, 40 mmol) in anhydrous tetrahydrofuran (150 ml) is treated dropwise with the solution of sodium diethylphosphite generated above. The reaction mixture is stirred 6.5 hours at room temperature, and then quenched with water and diluted with diethyl ether. The diethyl ether layer is separated, washed with water (2×100 ml), and dried over magnesium sulfate. After filtration and evaporation, the residue is chromatographed over silica gel (ethyl acetate as eluant) to give a clear oil (1.8 g).

In a process analogous to Example A using appropriate starting materials the following compounds are prepared:

EXAMPLE Aa

Diethyl[[3-(bromomethyl)phenyl]methyl]phosphonate.

EXAMPLE Ab

Diethyl[[4-(bromomethyl)phenyl]methyl]phosphonate.

EXAMPLE B

Ethyl N-(3-bromophenyl)glycinate.

A solution of meta-bromoaniline (10 g, 58 mmol) ethyl bromoacetate (10 g, 60 mmol), triethylamine (5 ml) and 4-dimethylaminopyridine (0.2 g) in ethanol (50 ml) is refluxed overnight. The solution is cooled in an ice bath and the crystals which form are collected by filtration and washed with methanol to give 8 g of white crystals.

In a process analogous to Example B using appropriate starting materials the following compound is prepared:

EXAMPLE Bb

Ethyl N-(2-bromophenyl)glycinate.

EXAMPLE C

Methyl N-[(3-bromophenyl)methyl]glycinate.

A solution of 3-bromobenzylbromide (4.3 g, 17.2 mmol) in methanol (25 ml) and triethylamine (5 ml) is treated with glycine methyl ester hydrochloride (4.3 g, 34.4 mmol) and heated to reflux for 18 hours. The solvent is removed in vacuo and the residue chromatographed over silica gel (0–2% methanol in ethyl acetate as eluant) to give 1.62 g of a yellow oil.

EXAMPLE D

Diethyl[[3-(2-aminoethyl)phenyl]methyl]phosphonate

STEP A: Preparation of Diethyl[[3-(cyanomethyl)phenyl]methyl]phosphonate,

A solution of diethyl[[3-(bromomethyl)phenyl]methyl]phosphonate (Example Aa) (7.0 g, 21.8 mmol) in acetone (25 ml) is treated with sodium iodide (0.33 g) which forms a precipitate. A solution of potassium cyanide (2.1 g, 32.7 mmol) in water (7.5 ml) is added and the reaction mixture heated to reflux for 30 minutes. The acetone is removed by evaporation and the aqueous phase extracted with ethyl acetate. The organic phase is dried over magnesium sulfate, filtered and evaporated, and the residue purified over silica gel to give an oil (3.7 g).

STEP B: Preparation of Diethyl[[3-(2-aminoethyl)phenyl]methyl]phosphonate

A solution of diethyl[[3-(cyanomethyl)phenyl]methyl]phosphonate in methanolic ammonia is reduced under a hydrogen atmosphere (50 psi) with Raney nickel as catalyst. The solvent is evaporated to give an oil (4.1 g).

EXAMPLE E

Diethyl(4-bromo-2-butenyl)phosphonate.

A solution of 1,4-dibromo-2-butene (20 g, 93.5 mmol) and triethylphosphite (23.7 g, 142.6 mmol) is heated at 85° C. under reduced pressure for four hours. The reaction mixture is purified directly on silica gel using ethyl acetate as eluant to give 14 g of a clear oil.

EXAMPLE F 4-(Diethylphosphonyl)-3-butenyl methanesulfonate, Mixture of E and Z Forms.

STEP A: Preparation of Tetrahydro-2-(3-butynyloxy)2H-pyran

A solution of 3-butyn-1-ol (74.5 g, 1.06 mol) in carbon tetrachloride (225 ml) is cooled in an ice bath, and treated with concentrated hydrochloric acid (1 ml). Dihydropyran (157 g, 1.86 mol) is then added via a dropping funnel. After stirring 16 hours the reaction mixture is treated with solid sodium bicarbonate for 30 minutes and filtered. The reaction mixture is concentrated and the residue is distilled in vacuo to give the title compound.

STEP B: Preparation of [4-[(Tetrahydro-2H-pyran2-yl)oxy]-1-butynyl]-phosphonic acid, diethyl ester A solution of tetrahydro-2-(3-butynyloxy)2H-pyran (20 g, 0.13 mol) in anhydrous tetrahydrofuran (200 ml) is cooled in a dry ice-acetone bath and treated dropwise with n-butyllithium (2.5M in hexane, 0.13 mol) in tetrahydrofuran (20 ml). The anion is stirred for 30 minutes and treated with diethyl chlorophosphate in tetrahydrofuran added via a slow stream. The reaction mixture is stirred 15 minutes and then warmed to room temperature overnight. A saturated aqueous solution of sodium bicarbonate (125 ml) is added and the mixture extracted with ethyl acetate (2×150 ml). The organic layer is separated, dried (magnesium sulfate), filtered and evaporated. The residue is chromatographed over silica gel and eluted with ethyl acetate in chloroform to give the title compound.

STEP C: Preparation of Diethyl(4-hydroxy-1-butynyl) phosphonic acid

The tetrahydropyranyl group is removed from [4-[(tetrahydro-2H-pyran-2-yl)oxy-1-butynyl]phosphonic acid, diethyl ester (20 g, 69 mmol) in methanol (500 ml) by reacting with para-toluene sulfonic acid (1.6 g) overnight. The solvent is evaporated and the residue dissolved in chloroform, washed with a saturated aqueous solution of sodium bicarbonate, dried (magnesium sulfate), filtered and evaporated. The residue is purified by silica gel chromatography and eluted with ethyl acetate in chloroform to give 6.4 g of the title compound.

STEP D: Preparation of 4-(Diethylphosphonyl)-3-butynyl, methanesulfonate

A solution of diethyl(4-hydroxy-1-butynyl)phosphonic acid (6.3 g, 30.6 mmol) in methylene chloride (30 ml) under nitrogen is cooled in an ice bath and treated with triethylamine (5 ml). A solution of methanesulfonyl chloride (3.9 g, 34 mmol) in methylene chloride (10 ml) is added dropwise. The reaction mixture is warmed over 16 hours to room temperature and quenched with water (125 ml). The aqueous layer is extracted with methylene chloride (2×100 ml) and the combined organic layers dried over magnesium sulfate, filtered and evaporated. The oil is chloroform as eluant) to give a light yellow oil (7 g).

STEP E: Preparation of 4-(Diethylphosphonyl)-3-butenyl methanesulfonate, Mixture of E and Z Forms A solution of 4-(diethylphosphonyl)-3-butynyl methanesulfonate (5 g, 17.6 mmol) in 9:1 tetrahydrofuran and pyridine is reduced under a hydrogen atmosphere (50 psi) with 10% palladium on barium sulfate as catalyst. The filtrate is evaporated to a yellow oil (5.2 g) and purified on silica gel (0–1% methanol in chloroform as eluant) to give a clear oil (3.15 g).

EXAMPLE G

Diethyl (2-bromoethyl)thiomethylphosphonate.

STEP A: Preparation of Diethoxyphosphinylmethyl thioacetate

A solution of tetra-n-butylammonium thioacetate (12.8 g, 0.041 mol) and diethyl chloromethylphosphonate (5 g, 0.027 mol) is stirred in tetrahydrofuran (30 ml) overnight at room temperature. After evaporation of the solvent, the residue is purified by silica gel chromatography (2:1 heptane:acetone as eluant) to give diethoxyphosphinylmethylthioacetate (4.3 g). $^1$H-NMR: 4H, m, 4.20–4.11 ppm; 2H, d, 3.23; 3H, s, 2.40; 6H, m, 1.33.

STEP B: Preparation of Diethyl (2-bromoethyl)thiomethylphosphonate

A solution of diethoxyphosphinylmethylthioacetate (4 g, 17.7 mol) in anhydrous methanol (50 ml) is treated with sodium methoxide (11.8 ml of 1.5M solution in methanol, 17.7 mol) and the solution is stirred in an ice bath for 2 hours. The reaction mixture is added slowly to dibromoethane (10 g, 53.1 mmol) in anhydrous methanol (50 ml) that is cooled in an ice bath. The solvent is evaporated and the residue dissolved in methylene chloride and the solution is washed with water. The organic layer is separated, dried over sodium sulfate, filtered and evaporated, and the residue is purified by silica gel chromatography (2:1 heptane:acetone as eluant) to give diethyl (2-bromoethyl)thiomethylphosphonate. $^1$H-NMR: 4H, m, 4.21–4.09 ppm; 2H, t, 3.53; 2H, t, 3.12; 2H, d, 2.86; 6H, m, 1.36–1.29.

We claim:

1. A compound of Formula I

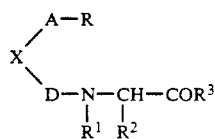

wherein X is
—CH$_2$CH$_2$—,
—CH=CH—,

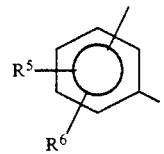

wherein $R^5$ and $R^6$ are independently selected from hydrogen, lower alkyl, phenyl, phenyl substituted by one to four substituents selected from lower alkyl of from one to six carbon atoms, lower alkoxy of from one to six carbon atoms, halogen or trifluoromethyl, phenyl lower alkyl, phenyl lower alkyl substituted by one to four substituents selected from lower alkyl of from one to six carbon atoms, lower alkoxy of from one to six carbon atoms, halogen or trifluoromethyl, lower alkoxy, lower alkylthio, halogen, hydroxy, or trifluoromethyl,

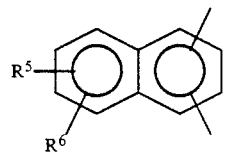

wherein $R^5$ and $R^6$ are as defined above,

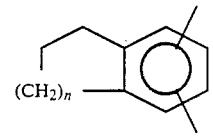

wherein n is 1 to 3, or

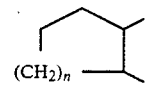

wherein n is as defined above; A and D are independently selected from —(CH$_2$)$_m$—, wherein m is 0 to 3, —CH=CH—, or —CH=CHCH$_2$—;

R is —OPO$_3$R$^7$R$^8$, wherein R$^7$ and R$^8$ are independently selected from hydrogen, lower alkyl, lower alkenyl, phenyl, phenyl substituted by one to four substituents selected from lower alkyl of from one to six carbon atoms, lower alkoxy of from one to six carbon atoms, halogen or trifluoromethyl, phenyl lower alkyl, phenyl lower alkyl substituted by one to four substituents selected from lower alkyl of from one to six carbon atoms, lower alkoxy of from one to six carbon atoms, halogen or trifluoromethyl, or a pharmaceutically acceptable labile group, —PO$_3$R$^7$R$^8$, wherein R$^7$ and R$^8$ are as defined above, or —PO$_2$R$^7$R$^8$, wherein R$^7$ and R$^8$ are as defined above;

R$^1$ is hydrogen, lower alkyl, lower alkenyl, phenyl lower alkyl, phenyl lower alkyl substituted by one to four substituents selected from lower alkyl of from one to six carbon atoms, lower alkoxy of from one to six carbon atoms, halogen or trifluoromethyl, —CO—alkyl,

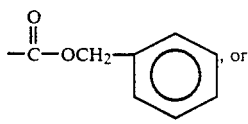, or

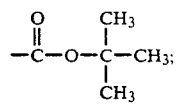

$R_2$ is hydrogen, $-CH_3$, $-CH_2OH$, $-CH_2-CO_2H$, $-CH_2-CONH_2$, $-CH_2CH_2-CO_2H$, $-CH_2CH_2-CONH_2$, $-CH_2SH$,

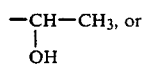

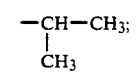

$R_3$ is $-OR^7$, wherein $R^7$ is as defined above, or $-NR^9R^{10}$, wherein $R^9$ and $R^{10}$ are independently selected from hydrogen, lower alkyl, lower alkenyl, phenyl, phenyl substituted by one to four substituents selected from lower alkyl of from one to six carbon atoms, lower alkoxy of from one to six carbon atoms, halogen or trifluoromethyl, phenyl lower alkyl, phenyl lower alkyl substituted by one to four substituents selected from lower alkyl of from one to six carbon atoms, lower alkoxy of from one to six carbon atoms, halogen or trifluoromethyl, or a pharmaceutically acceptable labile group; or a pharmaceutically acceptable salt thereof.

2. A compound according to claim 1 in which X is $-CH_2CH_2-$, $-CH=CH-$, or

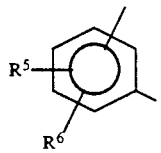

wherein $R^5$ and $R^6$ are independently selected from hydrogen, lower alkyl, phenyl, phenyl substituted by one to four substituents selected from lower alkyl of from one to six carbon atoms, lower alkoxy of from one to six carbon atoms, halogen or trifluoromethyl, phenyl lower alkyl, phenyl lower alkyl substituted by one to four substituents selected from lower alkyl of from one to six carbon atoms, lower alkoxy of from one to six carbon atoms, halogen or trifluoromethyl, lower alkoxy, lower alkylthio, halogen, hydroxy, or trifluoromethyl;

R is $-PO_3R^7R^8$, wherein $R^7$ and $R^8$ are independently selected from hydrogen, lower alkyl, lower alkenyl, phenyl, phenyl substituted by one to four substituents selected from lower alkyl of from one to six carbon atoms, lower alkoxy of from one to six carbon atoms, halogen or trifluoromethyl, phenyl lower alkyl, phenyl lower alkyl substituted by one to four substituents selected from lower alkyl of from one to six carbon atoms, lower alkoxy of from one to six carbon atoms, halogen or trifluoromethyl, or a pharmaceutically acceptable labile group;

$R^2$ is hydrogen,

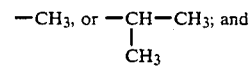

$R^3$ is $-OR^7$, wherein $R^7$ is as defined above.

3. A compound according to claim 2, in which X is $-CH_2CH_2-$, $-CH=CH-$, or

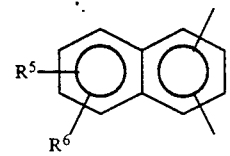

wherein $R^5$ and $R^6$ are independently selected from hydrogen, lower alkyl, phenyl, phenyl substituted by one to four substituents selected from lower alkyl of from one to six carbon atoms, lower alkoxy of from one to six carbon atoms, halogen or trifluoromethyl, phenyl lower alkyl, phenyl lower alkyl substituted by one to four substituents selected from lower alkyl of from one to six carbon atoms, lower alkoxy of from one to six carbon atoms, halogen or trifluoromethyl, lower alkoxy, lower alkylthio, halogen, hydroxy, or trifluoromethyl; and $R^1$ is hydrogen.

4. A compound according to claim 3 selected from the group consisting of:
   N-[[3-(phosphonomethyl)phenyl]methyl]glycine, hydrochloride;
   N-[2-[3-(phosphonomethyl)phenyl]ethyl]glycine, monohydrochloride;
   N-[[4-(phosphonomethyl)phenyl]methyl]glycine, monohydrochloride;
   N-(4-phosphono-2-butenyl)glycine, monohydrochloride;
   N-(4-phosphono-2-butenyl)-DL-alanine, monohydrochloride; and
   N-(4-phosphono-3-butenyl)glycine, diammonium salt (mixture of E and Z isomers).

5. A method of treating cerebrovascular disorders responsive to the blockade of glutamic acid or aspartic acid receptors in a mammal comprising administering to a mammal in need thereof a therapeutic effective amount of a compound according to claim 1 or a pharmaceutical composition comprising said compound.

6. A pharmaceutical composition for the treatment of cerebrovascular disorders responsive to the blockade of glutamic acid or aspartic acid receptors in mammals comprising a therapeutic effective amount of a compound according to claim 1 in combination with a pharmaceutically acceptable carrier.

* * * * *